(12) United States Patent
Okano et al.

(10) Patent No.: US 8,182,739 B2
(45) Date of Patent: May 22, 2012

(54) PROCESS FOR PRODUCING CONCENTRIC-CIRCULAR-GRADIENT FUNCTIONAL MATERIAL FOR BIOGENIC USE AND APPARATUS FOR PRODUCING THE SAME

(75) Inventors: Michiharu Okano, Tokyo (JP); Hiroshi Izui, Tokyo (JP)

(73) Assignee: Nihon University, Tokyo (JP)

(*) Notice: Subject to any disclaimer, the term of this patent is extended or adjusted under 35 U.S.C. 154(b) by 987 days.

(21) Appl. No.: 12/139,105

(22) Filed: Jun. 13, 2008

(65) Prior Publication Data
US 2008/0260565 A1 Oct. 23, 2008

Related U.S. Application Data

(63) Continuation of application No. PCT/JP2006/324805, filed on Dec. 13, 2006.

(30) Foreign Application Priority Data

Dec. 13, 2005 (JP) ................................. 2005-359196

(51) Int. Cl.
*B22F 7/00* (2006.01)

(52) U.S. Cl. .................. 419/6; 419/10; 419/32; 419/52; 266/251

(58) Field of Classification Search .................... 419/32, 419/6
See application file for complete search history.

(56) References Cited

U.S. PATENT DOCUMENTS

| 3,780,418 A | * | 12/1973 | Hurst | 419/42 |
| 6,203,752 B1 | * | 3/2001 | Bewlay et al. | 419/6 |
| 2006/0263231 A1 | * | 11/2006 | Groh et al. | 419/6 |

FOREIGN PATENT DOCUMENTS

| JP | 63-026301 | | 2/1988 |
| JP | 01154707 A | * | 6/1989 |
| JP | 2000-128651 | | 5/2000 |
| JP | 2001-154707 | | 6/2001 |
| JP | 2001-259017 | | 9/2001 |
| JP | 2002-309323 | | 10/2002 |

OTHER PUBLICATIONS

English Translation of JP63-026301 (Japanese pub. date Mar. 2, 1988), Funakoshi et al.*

* cited by examiner

*Primary Examiner* — Roy King
*Assistant Examiner* — Christopher Kessler
(74) *Attorney, Agent, or Firm* — Ditthavong Mori & Steiner, P.C.

(57) ABSTRACT

A concentric-circular-gradient functional material for biogenic use is produced using first, second, third and forth cylindrical partitions, and a cylindrical dice which are concentrically stood on a supporting stand. Ti powder (A) fills the first cylindrical partition. A first mixed powder including Ti powder (A) and biogenic material powder (B) fills between the first and second cylindrical partitions. A second mixed powder including a smaller amount of Ti powder (A) than the first mixed powder fills between the second and third cylindrical partitions. A third mixed powder including a smaller amount of Ti powder (A) than the second mixed powder fills between the third and fourth cylindrical partitions. The biogenic material powder (B) fills between the fourth cylindrical partition and the dice. The first to fourth partitions are pulled out. The dice is capped using a punch. The powders are sintered using a discharge plasma sintering machine.

12 Claims, 6 Drawing Sheets

PROCESS FOR PRODUCING CONCENTRIC-CIRCULAR-GRADIENT FUNCTIONAL MATERIAL FOR BIOGENIC USE AND APPARATUS FOR PRODUCING THE SAME

CROSS-REFERENCE TO RELATED APPLICATIONS

This application is a continuation application of PCT/JP2006/324805 filed Dec. 13, 2006, which claims priority of Japanese Patent Application No. 2005-359196 filed Dec. 13, 2005. The contents of these patent applications are incorporated herein by reference in their entirety.

BACKGROUND OF THE INVENTION

1. Field of the Invention

The present invention relates to a process for producing a concentric-circular-gradient functional material having a functional layer gradient in the radial direction, and an apparatus therefore.

2. Discussion of the Background

Hydroxyapatite (HAp), which is a kind of calcium phosphate, is similar to the inorganic component of bone in structure, and has an excellent biocompatibility; therefore, sintered bodies of hydroxyapatite are used as artificial bones, artificial dental roots, and other materials for biogenic use.

However, sintered bodies of hydroxyapatite are low in mechanical properties, such as toughness, in order to be used as materials for biogenic use. Accordingly, the sintered bodies of hydroxyapatite are very easily broken, so that the material is unable to be used as a reliable material.

Thus, in order to overcome a drawback of hydroxyapatite material, which is low in mechanical properties, such as toughness, the following method has been hitherto performed: a method of coating the surface of titanium with hydroxyapatite by plasma spray coating or the like, or a method of preparing a composite sintered material made of titanium and hydroxyapatite, or compounding hydroxyapatite with some other different material, thereby improving the mechanical properties.

However, the spray coating has a problem that when hydroxyapatite is sprayed, the crystal thereof is decomposed due to high temperature in the spraying so as to be made amorphous, whereby the biocompatibility peculiar to hydroxyapatite is removed. The spray coating also has a problem that the coating made of hydroxyapatite is easily peeled from titanium.

According to the sintering method, it is difficult to produce a composite sintered material made of titanium and hydroxyapatite since titanium and hydroxyapatite are different from each other in sintering temperature.

However, Japanese Patent Application Publication No. 2000-128651 discloses that the discharge plasma sintering method is used to sinter titanium and hydroxyapatite, titanium and hydroxyapatite are sufficiently sintered without the advance of the decomposition of hydroxyapatite in the coexistence of titanium and hydroxyapatite; thus, suggested is a composite sintered material wherein a mixed layer containing hydroxyapatite and titanium and a titanium layer are arranged in a concentric circular form, and Japanese Patent Application Publication No. 2001-259017 discloses a three-layered composite sintered material for biogenic use having titanium as a central material, calcium phosphate as a peripheral material, and an intermediate layer between the titanium and the calcium phosphate, wherein the composition of the two components is varied in a gradient form in the intermediate layer and the intermediate layer has a relative density of 90% or more.

However, the two-layered or three-layered composite sintered material has a problem that the material is easily cracked by a difference in thermal expansion coefficient which is generated when raw materials for the sintered material are sintered.

Japanese Patent Application Publication No. 2002-309323 discloses a process for producing a gradient functional material, in which a mixed layer having a stepwise or continuously varied ratio of components is arranged as an intermediate layer between inner and outer layers in order to in order to reduce stress due to thermal expansion when a sintered material having different thermal expansion coefficients is produced.

According to this method, however, at the time of producing a concentric-circular-gradient functional material, it is difficult to form an intermediate layer wherein the ratio of components is varied. About a method for forming such an intermediate layer easily, no specific disclosure is found.

SUMMARY OF THE INVENTION

According to one aspect of the present invention, a concentric-circular-gradient functional material for biogenic use is produced. A first cylindrical partition is stood on a supporting stand at a central portion thereof. A Ti powder (A) for a central portion is filled into the first cylindrical partition. Outside the first cylindrical partition, a second cylindrical partition having a larger diameter than that of the first cylindrical partition is concentrically stood on the supporting stand. A first mixed powder including the Ti powder (A) for a central portion and a biogenic material powder (B) for a surface layer portion is filled into a space confined by the outside of the first cylindrical partition and the inside of the second cylindrical partition. Outside the second cylindrical partition, a third cylindrical partition having a larger diameter than that of the second cylindrical partition is concentrically stood on the supporting stand. A second mixed powder which is smaller in the blended amount of the Ti powder (A) for a central portion than the first mixed powder is filled into a space confined by the outside of the second cylindrical partition and the inside of the third cylindrical partition. Outside the third cylindrical partition, a fourth cylindrical partition having a larger diameter than that of the third cylindrical partition is stood. A third mixed powder which is smaller in the blended amount of the Ti powder (A) for a central portion than the second mixed powder is filled into a space confined by the outside of the third cylindrical partition and the inside of the fourth cylindrical partition. Outside the fourth cylindrical partition, a cylindrical dice having a larger diameter than that of the fourth cylindrical partition is concentrically stood on the supporting stand. The biogenic material powder (B) for a surface layer portion is filled into a space confined by the outside of the fourth cylindrical partition and the inside of the cylindrical dice. The first to fourth cylindrical partitions are pulled out. The upper of the cylindrical dice is capped by use of a cylindrical punch. The dice and the supporting stand are turned upside down, and the supporting stand is removed. The dice is capped by use of a punch. The powders that fill the inside of the dice and the punches are sintered by use of a discharge plasma sintering machine.

According to another aspect of the present invention, a process for producing a concentric-circular-gradient functional material for biogenic use includes standing 4 or more cylindrical partitions having diameters different from each other concentrically on a supporting stand; standing, outside the cylindrical partition having the largest diameter, a cylindrical dice concentrically; filling a Ti powder (A) for a central portion into the cylindrical partition positioned at the center; filling a biogenic material powder (B) for a surface layer portion into a space confined by the outside of the cylindrical partition having the largest diameter and the inside of the cylindrical dice; filling a mixed powder comprising the Ti powder (A) for a central portion and the biogenic material powder (B) for a surface layer portion into each of the spaces confined by the cylindrical partitions, the mixed powder being a mixed powder wherein the blend ratio of the biogenic material powder (B) for a surface layer portion is made larger step by step from the inside to the outside; pulling out the cylindrical partitions; capping the upper of the cylindrical dice using a cylindrical punch; overturning the dice and the supporting stand upside down; removing the supporting stand; capping the upper of the dice using a punch; and sintering the powders with which the inside of the dice and the punches is filled using a discharge plasma sintering machine.

According to further aspect of the present invention, an apparatus for producing a concentric-circular-gradient functional material for biogenic use includes four or more cylindrical partitions, a cylindrical dice, and punches. The four or more cylindrical partitions are concentrically stood on a supporting stand and have diameters different from each other. The cylindrical dice is made of graphite. The supporting stand has, on the upper side thereof, a cylindrical projection having a size permitting the projection to be fitted onto the inside of the dice. Inside the projection, concentric circular and stepwise concaves are formed having sizes permitting the concaves to be fitted to the respective cylindrical partitions.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a view illustrating the structure of a supporting stand.

FIGS. 8 is a view illustrating a different example of the supporting stand.

DESCRIPTION OF THE EMBODIMENTS

The embodiments will now be described with reference to the accompanying drawings, wherein like reference numerals designate corresponding or identical elements throughout the various drawings.

An embodiment of the present invention provides a process for producing a concentric-circular-gradient functional material for biogenic use which is a process in which when a concentric circular composite sintered functional material is produced from biogenic materials such as titanium and hydroxyapatite, a mixed layer having a gradient composition is formed as an intermediate layer to prevent the composite material from being cracked when raw materials for the sintered material are sintered, and the mixed layer can easily be formed; and a producing apparatus therefore.

As a result of a research about a matter that when a concentric-circular-gradient functional material for biogenic use is sintered, the material is cracked, it was found that: in the case of forming at least three intermediate layers each having a gradient composition, the functional material can be prevented from being cracked when the material is sintered; and the intermediate layers each having a gradient composition can easily be molded by use of cylindrical partitions.

According to the process for producing a concentric-circular-gradient functional material for biogenic use, and an apparatus therefore of an embodiment of the invention, even in intermediate layers each made of a mixture of powders which are largely different from each other in density, such as titanium powder and hydroxyapatite powder, the layers can easily be molded as intermediate layers each having a gradient composition without separating the homogeneously mixed powders. The functional material can be prevented from being cracked, at the time of sintering the functional material, by forming three or more intermediate layers each having a gradient composition. Thus, a concentric-circular-gradient functional material excellent in mechanical properties can be obtained.

Researches were made on a process for producing a columnar biogenic material having a mechanical strength permitting the material to be put sufficiently into practical use, as a biomaterial suitable for artificial bone or the like, typical examples of which include hydroxyapatite; and an apparatus for producing the material. As a result, it was found that in the case of compounding a biomaterial such as hydroxyapatite and a different material such as titanium into a columnar form, interposing, as intermediate layers between the two layers, three or more composition-gradient layers wherein the blend ratio of the biomaterial and the different material is stepwise varied to form a molded body, and then sintering the molded body by a discharge plasma sintering method to prepare a concentric-circular-gradient functional material for biogenic use, the prepared material can be obtained as a concentric-circular-gradient functional material for biogenic use which can be sintered without being cracked, and exhibits excellent mechanical properties and toughness.

The material that is most frequently used as a biomaterial is hydroxyapatite (HAp), which is a kind of calcium phosphate. Hydroxyapatite is a compound represented by a chemical formula of $Ca_{10}(PO_4)_6(OH)_2$, and is a main component of human bone. Besides hydroxyapatite, tertiary calcium phosphate (β-TCP), which has not any hydroxyl group, is known.

In the embodiment of the present invention, hydroxyapatite powder or tertiary calcium phosphate is used as the biogenic material powder (B) for surface layer portion.

Titanium powder is used as the powder (A) for a central portion, which is powder of a different material. About titanium, metal ions thereof do not elute out in body fluid; thus, titanium is harmless for living bodies. When titanium is used as the center portion of a concentric circular composite body, the mechanical strength thereof can be improved.

It is also allowable to use, instead of the simple substance of titanium, titanium powder containing a biogenic material powder so as to set the ratio by volume of the biogenic material powder to 50% or less after the mixed powder is sintered (to use a mixed powder made of 50% or less of a biogenic material powder and titanium powder). When the biogenic material powder is blended with titanium powder, the difference between the central portion and the intermediate layers in physical properties can be made small. However, if the biogenic material powder is blended to set a ratio by volume thereof to a value more than 50% after the mixed powder is sintered, the mechanical properties of titanium as the central material fall. Thus, the upper limit of the blended amount of the biogenic material powder is 50% by volume after the sintering.

As the powder (A) for a central portion, hydroxyapatite (HAp) powder may be used. In this case, it is preferred to use, as the biogenic material powder (B) for a surface layer portion, tertiary calcium phosphate (β-TCP). That is, tertiary calcium phosphate (β-TCP) is the most biocompatible so that the phosphate is completely absorbed into bone, but the phosphate is the lowest in mechanical strength; in order to improve this property, hydroxyapatite (HAp) is used in the central portion, as a scaffolding for osteoblastic cells, for the purpose of an improvement in the mechanical strength. Since hydroxyapatite (HAp) is not absorbed into bone, the material can be used as the central material. However, hydroxyapatite (HAp) is lower in mechanical strength than Ti, but it is more convenient from the viewpoint of biocompatibility that in parts for which a high strength is not required, hydroxyapatite (HAp) is used as the central material therefore. It has been able to be ascertained that when hydroxyapatite (HAp) is blended with tertiary calcium phosphate (β-TCP) to set the ratio by volume of hydroxyapatite to 50% when the mixed powder is sintered, the mechanical strength can be made about two times better.

It is necessary to form, as intermediate layers of the concentric-circular-gradient functional material for biogenetic use, the following layers between the central portion and the surface layer portion: three or more composition-gradient intermediate layers wherein about the blend ratio between the powder (A) for the central portion and the biogenic material powder (B) for the surface layer portion, the ratio of the biogenic material powder (B) for the surface layer portion is made larger toward the surface layer. If the number of the composition-gradient intermediate layers is less than 3, at the time of subjecting the powdery molded body to discharge plasma sintering a delamination or crack is generated by internal stress so that a good concentric-circular-gradient functional material for biogenetic use cannot be obtained. As the number of the intermediate layers is larger, the advantageous effects are larger. However, if the number is made too large, the production unfavorably becomes difficult. Additionally, the mechanical strength lowers. The maximum number of the intermediate layers, which depends on the size of the concentric-circular-gradient functional material, is about 8 from the viewpoint of practical use.

The inventors have made eager researches on plural processes for producing a concentric-circular-gradient functional material having three or more composition-gradient, intermediate layers (the total number of the layers is five or more). That is, the inventors have investigated various processes as a powder molding process for a concentric-circular-gradient functional material for biogenetic use.

First, the inventors have performed, for example, a process of pressing and hardening up layers one by one and successively stacking the layers. However, according to this process, wherein powder is filled into a space between two cylindrical mold parts and then the powder is pressed to form a cylindrical molded body, there is caused a problem that it is difficult to take out the molding parts (tools) after the pressing.

Figure 4:
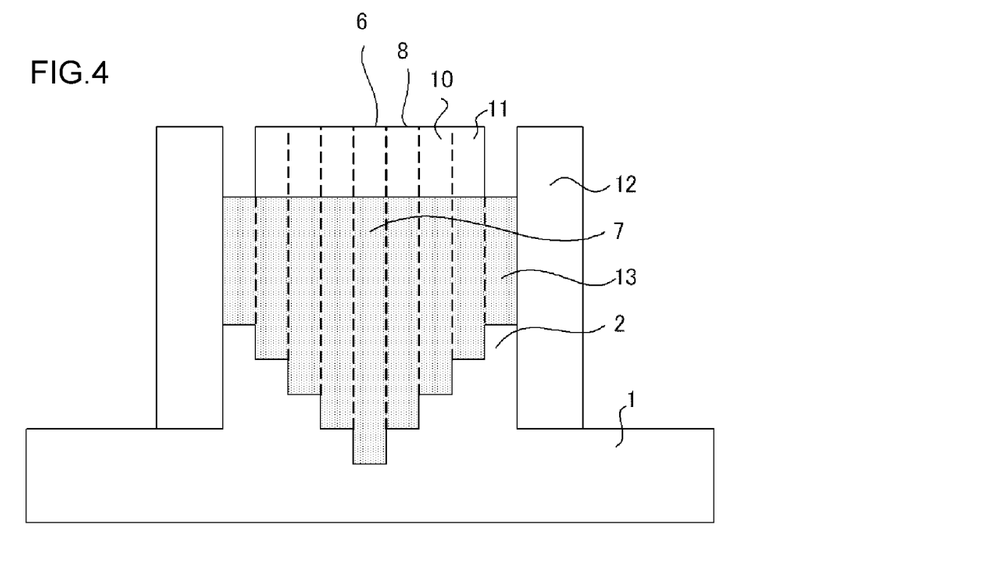
FIG. 4 is a view illustrating a situation that the first and the second cylindrical partitions, third and fourth cylindrical partitions, and a cylindrical dice are stood on the partition, and the titanium powder, the mixed powder/mixed powders, and hydroxyapatite powder are filled.

The inventors have investigated other processes also, and as a result, found that the best producing process is a process, as illustrated in FIG. 4, wherein cylindrical partitions are used, powder is filled into each of spaces between the cylindrical partitions, and then the cylindrical partitions (cylinders) are pulled out, thereby producing a concentric-circular-gradient functional material for biogenetic use.

This process has the following advantages: it is not particularly necessary to consider the particle diameter of the powder to be filled; a mixed powder wherein titanium powder and a biogenic material powder are homogeneously mixed can be molded while the mixture state is kept without separating the two powders: when members different from each other in diameter are prepared as the cylindrical partitions (tools), layers the number of which is selected at will can be formed; and the apparatus for the production is not required to have a complicated structure. However, the process has a drawback that the concentric circles are not kept in an even state; however, an especial problem for practical use is not caused for the performance itself of the resultant concentric-circular-gradient functional material for biogenetic use.

The discharge plasma sintering method is suitable for the sintering of the powdery molded body.

The discharge plasma sintering method (SPS process) is a process of applying direct current, to which a DC pulse current or a rectangular wave is applied, to electrodes in a vacuum or a nonoxidative atmosphere such as $N_2$ gas or Ar gas to perform sintering by use of a discharge phenomenon between powdery particles.

The surface of the powder is activated by the discharge, and further the oxide film is removed; thus, the powder can be sintered at lower temperature in a shorter time by conventional sintering methods.

For the sintering of Ti, a high temperature of 1300° C. or higher is required by conventional sintering methods. Hydroxyapatite can be sintered only at a low temperature of 1300° C. or lower. Thus, it is difficult to sinter a powdery molded body wherein the two are present together with each other by any conventional sintering method.

However, when the discharge plasma sintering method is used, the sintering temperature of titanium can be lowered to about 750° C. For this reason, when the discharge plasma sintering method is used as the method for sintering a composite body of titanium and hydroxyapatite, the composite body can be sintered.

On the basis of FIGS. 1 to 6, the following will describe a process for producing a concentric-circular-gradient functional material composed of plural layers, the total number of the layers being five, which has a central portion made of titanium, a surface layer portion made of hydroxyapatite, and an intermediate composed of three composition-gradient intermediate layers.

As a powder molding apparatus, prepared are a supporting stand, four cylindrical partitions having outer diameters different from each other, a cylindrical dice, and punches.

Figure 1A:
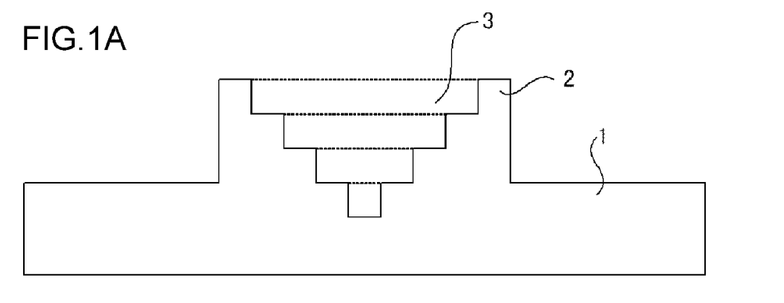
FIG. 1A is a front sectional view thereof and FIG. 1B is a plan view thereof.
Figure 1B:
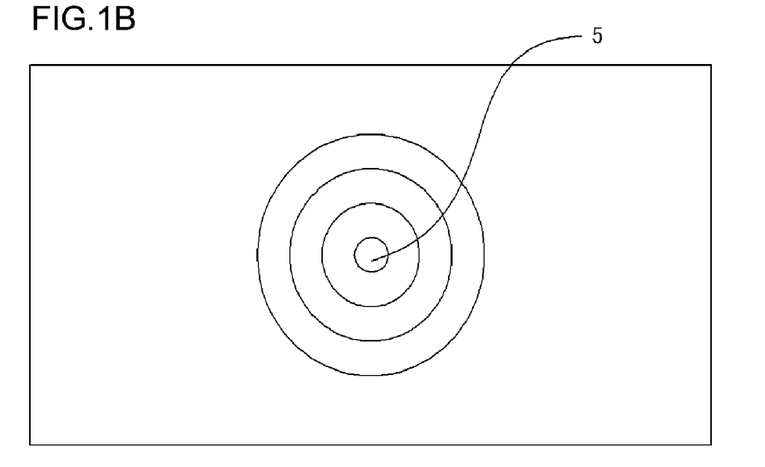

FIG. 1 is a view illustrating the structure of the supporting stand, and FIG. 1A is a front sectional view thereof and FIG. 1B is a plan view thereof. As illustrated in FIGS. 1A and 1B, the supporting stand 1 has, at the center thereof, a columnar projection 2 which can be fitted to the inside of the cylindrical dice, and has, inside the projection 2, concentric circular and stepwise concaves 3. The inner diameters of the individual stepwise concaves 3 are substantially equal to the respective outer diameters of the cylindrical partitions, which have the different outer diameters. The cylindrical partitions can be stood in the stepwise concaves, respectively.

In another modification example of the supporting stand, which is not illustrated, a columnar projection having concentric circular and stepwise convexes is formed instead of the columnar projection having the stepwise concaves.

In this case, the outer diameters of the concentric circular and stepwise convexes are equal to the respective inner diameters of the cylindrical partitions, which have the different outer diameters. The cylindrical partitions can be fitted to the respective convexes so as to be stood.

Figure 8A:
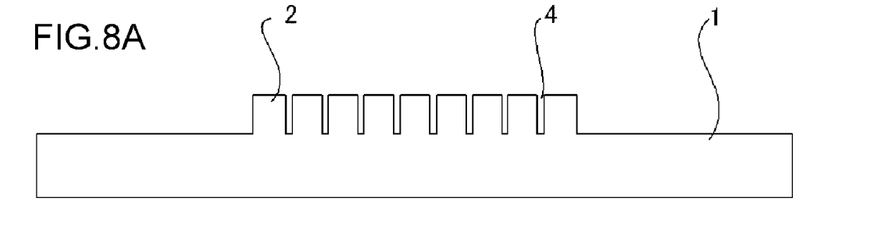
FIG. 8A is a front sectional view thereof and FIG. 8B is a plan view thereof.
Figure 8B:
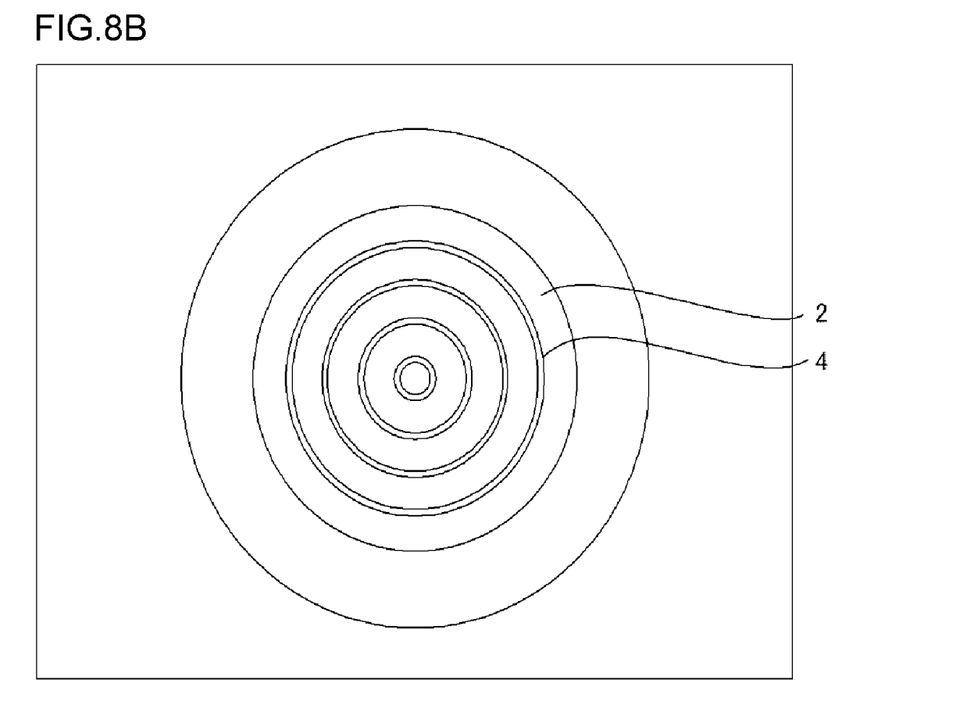
Figure 9:
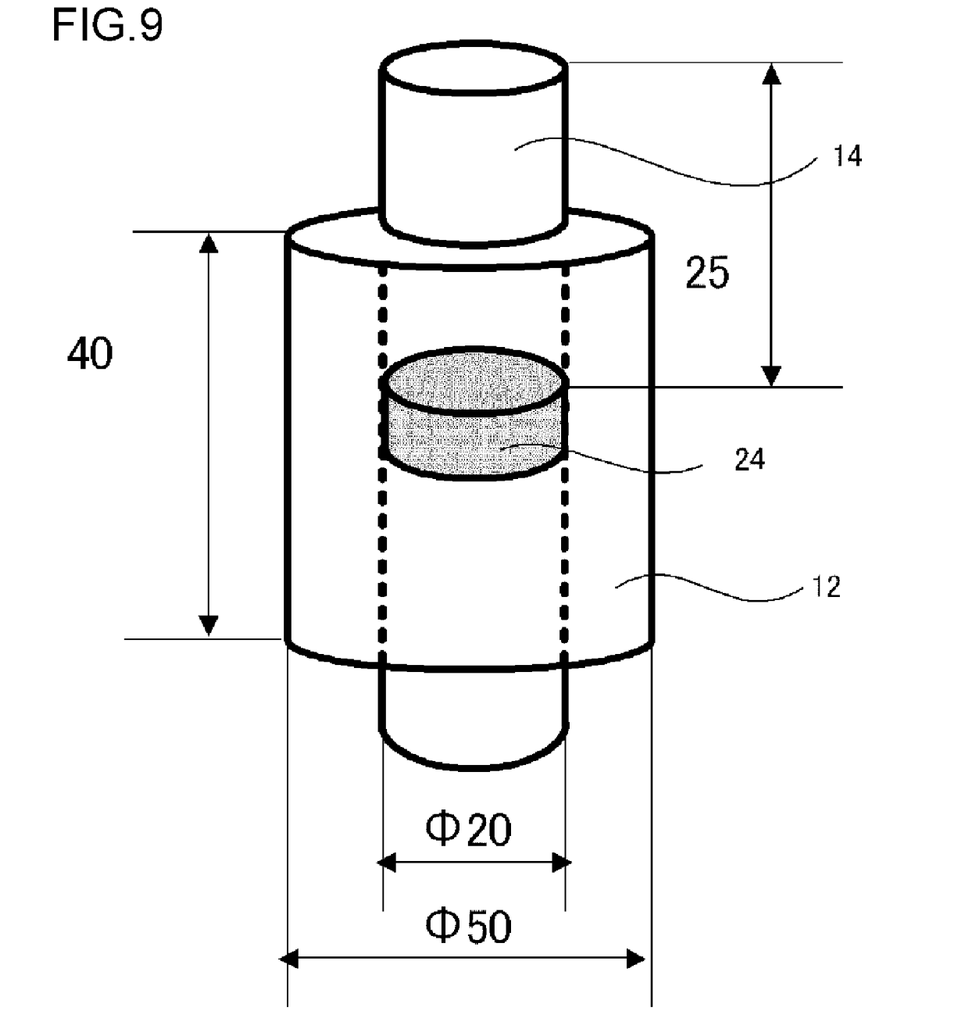
FIG. 9 is a view illustrating the dimensions of a dice and punches used in Examples.

As illustrated in FIGS. 8A and 8B, in still another modification example, a supporting stand 1 has, on the upper surface thereof, a columnar projection 2, and concentric circular grooves 4, into which the cylindrical partitions can be fitted, are made in the columnar projection 2. The outer diameters of the concentric circular grooves 4 are equal to the outer diameters of the cylindrical partitions, respectively. The widths of the concentric circular grooves are made substantially equal to or larger than the thicknesses of the cylindrical partitions, respectively.

When the concentric circular and stepwise concaves, concentric circular and stepwise convexes or concentric circular grooves are made in the columnar projection 2, the positioning of the cylindrical partitions on the supporting stand can be precisely and easily attained.

The material of the supporting stand is not particularly limited, and may be a metallic material such as Al, Zn, Mg, Ge, Cu, or an alloy thereof. The material is preferably Al, Zn, Mg or an alloy thereof, which is light.

The following will describe a process using the supporting stand illustrated in FIGS. 1A and 1B and having, inside its columnar projection, the concentric circular and stepwise concaves, to produce a concentric-circular-gradient functional material for biogenetic use which has a central portion made of titanium and a surface layer portion made of hydroxyapatite.

Figure 2:
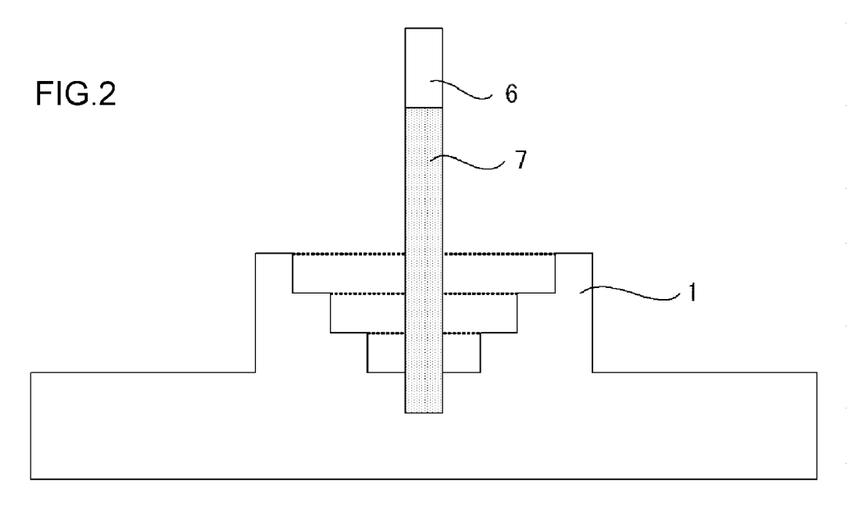
FIG. 2 is a view illustrating a situation that a first cylindrical partition is stood in a central concave in a supporting stand, and titanium powder, which becomes a first layer, is filled.

First, as illustrated in FIG. 2, a first cylindrical partition 6, which has the smallest outer diameter, is stood in a central concave 5 in the columnar projection of the supporting stand 1. Titanium powder 7 is then filled into the stood first cylindrical partition.

Figure 3:
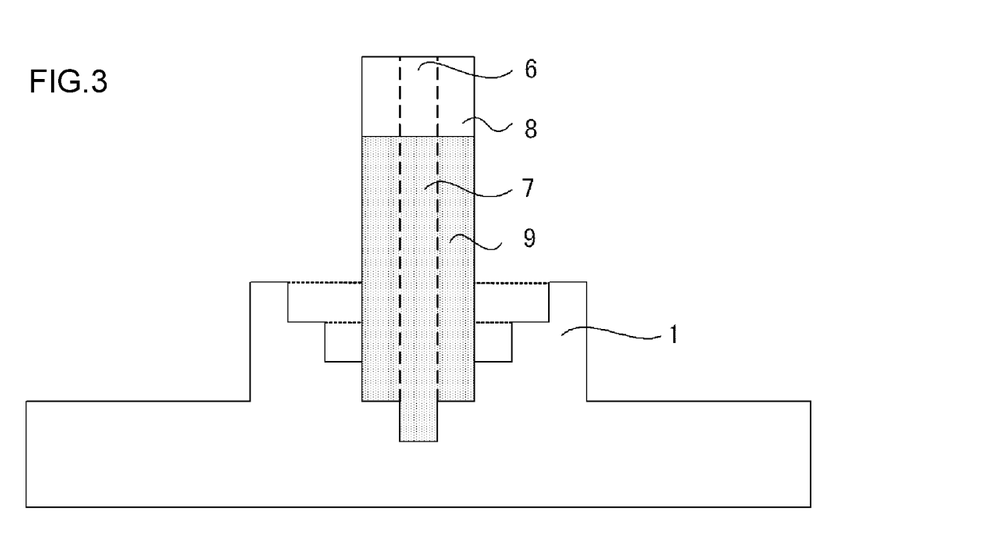
FIG. 3 is a view illustrating a situation that a second cylindrical partition is stood outside the first cylindrical partition, and a mixed powder, which becomes a second layer, is filled.

Next, as illustrated in FIG. 3, a second cylindrical partition 8, which has a larger inner diameter than the outer diameter of the first cylindrical partition 6, s stood in one out of stepwise concaves 3 in the supporting stand 1, and then a mixed powder (a) 9 composed of titanium powder and hydroxyapatite powder is filled into a space confined by the outside of the first cylindrical partition 6 and the inside of the second cylindrical partition 8.

Next, a third cylindrical partition 10, which has a larger inner diameter than the outer diameter of the second cylindrical partition 8, is stood in one of the stepwise concaves 3 in the supporting stand 1, and then a mixed powder (b) which is composed of hydroxyapatite powder and titanium powder and is smaller in blend ratio of titanium powder than the mixed powder (a) is filled into a space confined by the outside of the second cylindrical partition 8 and the inside of the third cylindrical partition 10.

Next, a fourth cylindrical partition 11, which has a larger inner diameter than the outer diameter of the third cylindrical partition 10, is stood in one of the stepwise concaves in the supporting stand, and then a mixed powder (c) which is composed of hydroxyapatite powder and titanium powder and is smaller in blend ratio of titanium powder than the mixed powder (b) is filled into a space confined by the outside of the third cylindrical partition 10 and the inside of the fourth cylindrical partition 11.

At last, a dice 12 made of graphite and having a larger inner diameter than the outer diameter of the fourth cylindrical partition 11 is fitted to the columnar projection 2 so as to be stood. Hydroxyapatite powder 13 is then filled into a space confined by the inside of the dice 12 and the outside of the cylindrical partition 11. It is preferred to set carbon paper as a releasing material onto the inner surface of the columnar graphite dice.

Thereafter, the four cylindrical partitions are pulled out. While the cylindrical partitions are rotated in the pulling, the cylindrical partitions are pulled out; as a result, the shape of the layers of the filled powders can be kept without causing the filled powders to adhere onto the cylindrical partitions. In this way, the layers from the central portion to the outer surface turn totally to five layers. Thus, a powdery molded body composed of the five layers in total is yielded wherein the central portion is made of titanium, the outer surface is made of hydroxyapatite, and the intermediate portion is made of the composition-gradient layers made of titanium and hydroxyapatite.

After the cylindrical partitions are pulled out, a carbon paper piece cut out into a circular form is used if necessary to cap the upper surface of the powdery molded body inside the dice. A punch made of graphite is inserted into the dice. Thereafter, the whole of the supporting stand and the dice into which the powders are filled are turned upside down.

The material of the cylindrical partitions is preferably a metallic material such as copper, copper alloy, and stainless steel. According to the use of the metallic material for the cylindrical partitions, the powders do not adhere easily thereto and the filling and the pulling-out of the cylindrical partitions become easy. Additionally, each of the partitions can keep the strength thereof even if the thickness thereof is made small.

Figure 5:
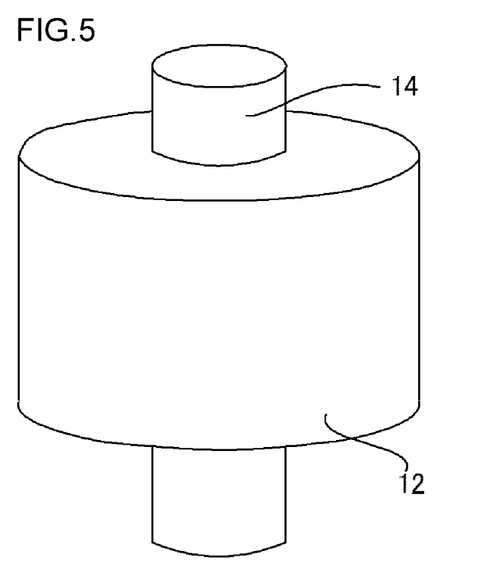
FIG. 5 is a view illustrating a situation that the filled powders are held inside the dice and punches.

The supporting stand is removed from the dice, and a carbon paper piece cut out into a circular form is used if necessary to cap the molded body. Another punch 14 made of graphite is inserted into the dice from the above thereof. Thus, as illustrated in FIG. 5, the molded body is made into a state that the molded body is capped with the punch 14, so as not to spill the powders filled into the dice.

Figure 6:
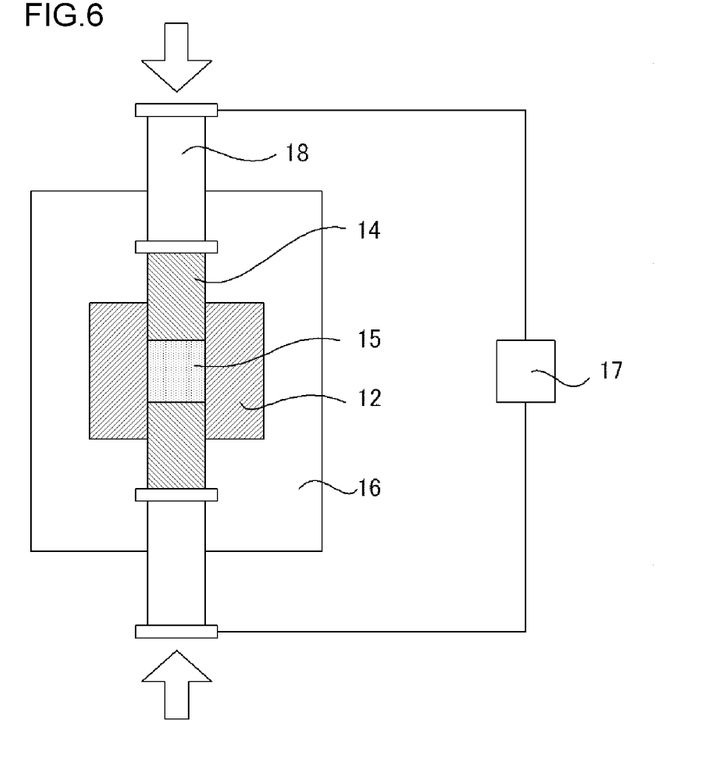
FIG. 6 is a view illustrating a situation that a discharge plasma sintering machine is used to perform sintering.
Figure 7:
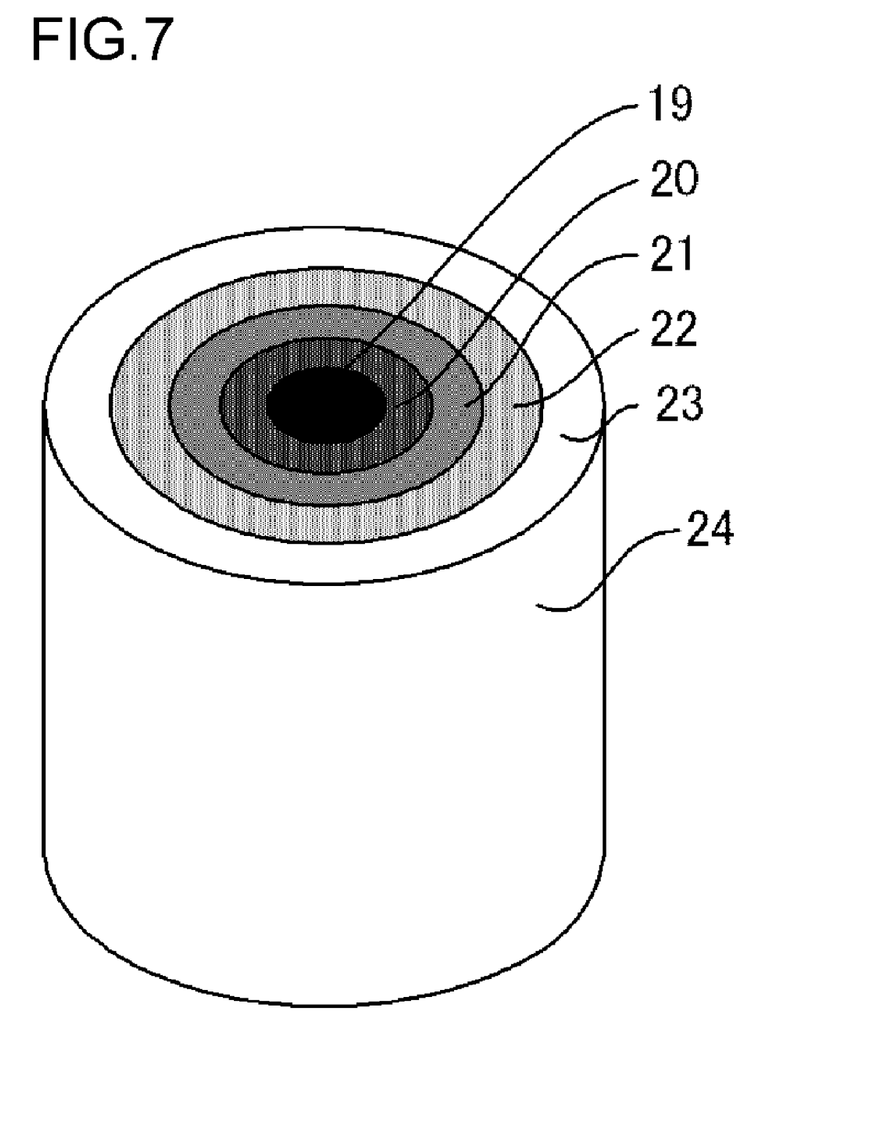
FIG. 7 is a view illustrating a concentric-circular-gradient functional material for biogenic use that is composed of layers the total number of which is five.

A pressing machine is used to apply a pressure of about 10 MPa preliminarily to the upper and lower graphite punches so as to turn the powders in the dice to a compact. Next, as illustrated in FIG. 6, the dice 12 and the punches 14, which contain therein the compact 15, are set into a vacuum chamber 16 of a discharge plasma sintering machine. A DC pulse current is applied from a power source 17 through a pressing ram 18 to the punches 14, and a discharge phenomenon between the powdery particles is used to sinter the compact. The resultant sintered body is taken away from the dice, and end faces of the sintered body are polished. Thus, as illustrated in FIG. 7, a concentric-circular-gradient functional material 24 for biogenetic use is produced, which is composed of a first layer 19 to a fifth layer 23 in total.

In the explained example, the step of standing a cylindrical partition at the central portion and filling powder is repeated from the central portion, thereby producing a composite body. However, an equivalent composite body can be produced by filling powder from the peripheral portion instead of performing the filling from the central portion, that is, by filling powder initially into a space confined by the inside of a dice and a fourth cylindrical partition, and then repeating an equivalent powder-filling step toward the center.

In another example, an equivalent composite body can be produced by: standing, initially, plural (four or more) cylindrical partitions different in diameter concentrically onto a supporting stand; standing a cylindrical dice concentrically outside the cylindrical partition having the largest diameter; filling a powder (A) for central portion into the cylindrical partition positioned at the center; filling a biogenic material powder (B) for surface layer portion into a space confined by the outside of the cylindrical partition having the largest diameter and the inside of the cylindrical dice; filling, into each of spaces confined by the plural cylindrical partitions, a mixed powder made of the powder (A) for central portion and the biogenic material powder (B) for surface layer portion wherein the blend ratio of the biogenic material powder (B) for surface layer portion is stepwise made larger from the inside toward the outside; and then pulling the cylindrical partitions.

EXAMPLES

The embodiment of the present invention will be described in detail by way of the following Examples.

As powder forming tools, prepared were a supporting stand made of aluminum, four cylindrical partitions, a dice made of graphite, and punches to produce a concentric-circular-gradient functional material for biogenetic use which was composed of five layers in total.

The used aluminum supporting stand was a supporting stand having, at the center thereof, a columnar projection, and having, inside the projection, stepwise concaves as illustrated in FIG. 1.

The sizes and the materials of the four cylindrical partitions stood in the aluminum supporting stand are as shown in Table 1.

TABLE 1

|  | Cylinder [mm] between first and second layers | Cylinder [mm] between second and third layers | Cylinder [mm] between third and fourth layers | Cylinder [mm] between fourth and fifth layers |
|---|---|---|---|---|
| Diameter | 4 | 8 | 12 | 16 |
| Length | 105 | 95 | 85 | 75 |
| Thickness | 0.1 | 0.3 | 0.5 | 0.5 |
| Material | Brass | SUS304T | Brass | Brass |

The dice and the punches were made of high-strength graphite, and the dimension of the dice was as follows: inner diameter: 20 mm, outer diameter: 50 mm, and height: 40 mm. The punches were each a column having an outer diameter of 20 mm and a height of 25 mm.

In order to obtain a concentric-circular-gradient functional material composed of five layers in total and having strength and a natural or function as a scaffolding for osteoblastic cells beside biocompatibility, Ti powder was used as a core material (first layer) as illustrated in FIG. 7, and hydroxyapatite or tertiary calcium phosphate powder was used for an outer surface layer (fifth layer). Between the two were arranged composition-gradient layers wherein the composition ratio of the two in the mixed powder was stepwise gradient (second to fourth layers).

About sample materials, pure titanium having an average particle diameter of 63 to 90 µm and a purity of 99.9% was used as the Ti powder. When the particle diameter of Ti powder is large, the Ti powder is unevenly mixed with hydroxyapatite powder or tertiary calcium phosphate powder so that the Ti powder is separated. Therefore, in order to mix the powders evenly, the particle diameter is preferably from about 63 to 90 µm.

As the hydroxyapatite (HAp) powder, a powder SHAp-100 manufactured by Taihei Chemical Industrial Co., Ltd. was used. This powder is a powder made of a substance represented by a chemical formula of $Ca_{10}(PO_4)_6(OH)_2$, having a white appearance, and having the following properties: particle diameter: 30 µm, particle diameter of primary particles: 0.2 to 0.3 µm, ratio by mole: 1.67, and molecular weight: 1004.64.

As the tertiary calcium phosphate (β-TCP) powder, a powder β-TCP manufactured by Taihei Chemical Industrial Co., Ltd. was used. This powder is a powder made of a substance represented by a chemical formula of $Ca_3(PO_4)_2$, having a white appearance, and having the following properties: particle diameter: 150 to 75 µm, ratio by mole: 1.50, and molecular weight: 310.18.

In the process for producing the concentric-circular-gradient functional material for biogenetic use, the first cylindrical partition was stood at the center of the supporting stand, and the first layer powder was filled thereinto. Next, the second cylindrical partition was stood outside the first cylindrical partition, and the second layer powder was filled into a space confined by the two. The third cylindrical partition, the fourth cylindrical partition and the dice were successively stood while the third layer powder, the fourth layer powder and the fifth layer powder were successively filled into the corresponding spaces, respectively. A carbon paper piece was fitted into the inner surface of the high-strength graphite dice in order to improve the peelability.

Subsequently, the cylindrical partitions were pulled out, and then a carbon paper piece was used to cap the filled powders. The filled powders were lightly compressed from the above thereof with one of the punches, which were high-strength punches made of graphite, so as to cap the filled powders. The whole was turned upside down, and then the supporting stand was removed. A carbon paper piece was used to cap the upper of the high-strength graphite dice, and the other high-strength graphite punch was used to compress the filled powders lightly from the above thereof to cap the powders.

The dice and the punches were set to a hand pressing machine, and the filled powders were lightly compressed.

Thereafter, the workpiece was set to a discharge plasma sintering machine, and an electric current was sent through the punches to the workpiece. In this way, the powders in the dice were sintered.

Conditions for the sintering were as shown in Table 2.

TABLE 2

| | |
|---|---|
| Filling pressure | 10[Mpa] |
| Temperature increasing rate | 100[° C./min] |
| Sintering time | 8[min] |
| Sintering temperature | 800[° C.] |
| Sintering pressure | 22.3[Mpa] |
| Cooling manner | Furnace cooling |

After the sintering, the sintered body was taken away from the dice. Since the individual layers were mixed with each other in both ends of the sintered body, each of the end faces was polished by means of a polishing machine until a face, wherein the composition was inclined over the five layers, made its appearance. In such a way, concentric-circular-gradient functional materials for biogenetic use were yielded. The component(s) and the ratio by volume of each of the layers in each of the yielded concentric-circular-gradient functional materials for biogenetic use are shown in Tables 3 to 6. Each of the proportions by volume represents the proportion by volume after the sintering.

Table 3 is concerned with an example wherein Ti powder was used as the central material (first layer) and hydroxyapatite was used as the biogenic material for the surface layer (fifth layer).

TABLE 3

| Layer | Sample material(s) | Ratio by volume [%] |
|---|---|---|
| First layer | Ti | 100 |
| Second layer | SHAp-100 | 60 |
| | Ti | 40 |
| Third layer | SHAp-100 | 80 |
| | Ti | 20 |
| Fourth layer | SHAp-100 | 95 |
| | Ti | 5 |
| Fifth layer | SHAp-100 | 100 |

Table 4 is concerned with an example wherein a mixed powder made of Ti powder and the hydroxyapatite powder (SHAp-100) was used as the central material (first layer) and hydroxyapatite powder was used as the biogenic material for the surface layer (fifth layer).

TABLE 4

| Layer | Sample material(s) | Ratio by volume [%] |
|---|---|---|
| First layer | SHAp-100 | 50 |
| | Ti | 50 |
| Second layer | SHAp-100 | 70 |
| | Ti | 30 |
| Third layer | SHAp-100 | 85 |
| | Ti | 15 |
| Fourth layer | SHAp-100 | 95 |
| | Ti | 5 |
| Fifth layer | SHAp-100 | 100 |

Table 5 is concerned with an example wherein a mixed powder made of Ti powder and tertiary calcium phosphate powder ($\beta$-TCP) was used as the central material (first layer) and tertiary calcium phosphate powder ($\beta$-TCP) was used as the biogenic material for the surface layer (fifth layer).

TABLE 5

| Layer | Sample material(s) | Ratio by volume [%] |
|---|---|---|
| First layer | $\beta$-TCP | 50 |
| | Ti | 50 |
| Second layer | $\beta$-TCP | 70 |
| | Ti | 30 |
| Third layer | $\beta$-TCP | 85 |
| | Ti | 15 |
| Fourth layer | $\beta$-TCP | 95 |
| | Ti | 5 |
| Fifth layer | $\beta$-TCP | 100 |

Table 5 is concerned with an example wherein the hydroxyapatite powder (SHAp-100) was used as the central material (first layer) and tertiary calcium phosphate powder ($\beta$-TCP) was used as the biogenic material for the surface layer (fifth layer).

TABLE 6

| Layer | Sample material(s) | Ratio by volume [%] |
|---|---|---|
| First layer | SHAp-100 | 100 |
| Second layer | SHAp-100 | 75 |
| | $\beta$-TCP | 25 |
| Third layer | SHAp-100 | 50 |
| | $\beta$-TCP | 50 |
| Fourth layer | SHAp-100 | 25 |
| | $\beta$-TCP | 75 |
| Fifth layer | $\beta$-TCP | 100 |

In Tables 3 to 6, the first layer (center), the second layer, the third layer, the fourth layer, and the fifth layer (outmost layer) are the layers positioned outwards in turn from the inside of the column. Table 3 is concerned with an example wherein Ti was used as the central material, the hydroxyapatite (SHAp-100) was used in the outer layer, and the intermediate layers were each a layer wherein the two were mixed. Table 5 is concerned with an example wherein Ti and tertiary calcium phosphate ($\beta$-TCP) were used in the same manner. Table 6 is concerned with an example wherein the hydroxyapatite (SHAp-100) was used at the center, tertiary calcium phosphate ($\beta$-TCP) was used in the outer layer, and the intermediate layers were each a layer wherein the two were mixed.

Each of the resultant concentric-circular-gradient functional materials for biogenetic use was not cracked when sintered, and it was a material good in mechanical properties.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A process for producing a concentric-circular-gradient functional material for biogenic use, comprising:
   standing a first cylindrical partition on a supporting stand at a central portion thereof;
   filling a Ti powder (A) for a central portion into the first cylindrical partition;
   standing, outside the first cylindrical partition, a second cylindrical partition having a larger diameter than that of the first cylindrical partition concentrically on the supporting stand;
   filling a first mixed powder comprising the Ti powder (A) for a central portion and a biogenic material powder (B) for a surface layer portion into a space confined by the outside of the first cylindrical partition and the inside of the second cylindrical partition;

standing, outside the second cylindrical partition, a third cylindrical partition having a larger diameter than that of the second cylindrical partition concentrically on the supporting stand;

filling a second mixed powder which is smaller in the blended amount of the Ti powder (A) for a central portion than the first mixed powder into a space confined by the outside of the second cylindrical partition and the inside of the third cylindrical partition;

standing, outside the third cylindrical partition, a fourth cylindrical partition having a larger diameter than that of the third cylindrical partition concentrically;

filling a third mixed powder which is smaller in the blended amount of the Ti powder (A) for a central portion than the second mixed powder into a space confined by the outside of the third cylindrical partition and the inside of the fourth cylindrical partition;

standing, outside the fourth cylindrical partition or an outermost cylindrical partition if additional cylindrical partitions are used, a cylindrical dice having a larger diameter than that of the fourth cylindrical partition or the outermost cylindrical partition concentrically on the supporting stand;

filling the biogenic material powder (B) for a surface layer portion into a space confined by the outside of the fourth cylindrical partition or the outermost cylindrical partition and the inside of the cylindrical dice;

pulling out all of the first to fourth cylindrical partitions;

capping the upper of the cylindrical dice using a cylindrical punch;

turning the dice and the supporting stand upside down;

removing the supporting stand;

capping the upper of the dice using a punch; and sintering the powders with which the inside of the dice and the punches are filled using a discharge plasma sintering machine, wherein the supporting stand has, on the upper side thereof, a plurality of cylindrical projections configured to permit the respective cylindrical partitions to stand therein.

2. The process for producing a concentric-circular-gradient functional material for biogenic use according to claim 1, wherein the number of the cylindrical partitions is set to five or more, and four or more composition-gradient intermediate layers, in which in the blend ratio of the Ti powder (A) for a central portion and the biogenic material powder (B) for a surface layer portion between the central portion and the surface layer portion, the ratio of the biogenic material powder (B) for a surface layer portion is made larger step by step toward the surface layer, are formed.

3. The process for producing a concentric-circular-gradient functional material for biogenic use according to of claim 1, wherein carbon paper is arranged as a releasing agent on the inside of each of the dice and the punches.

4. The process for producing a concentric-circular-gradient functional material for biogenic use according to claim 1, wherein filling the Ti powder (A) for a central portion comprises filling only Ti powder (A), or filling a mixed powder in which a biogenic material powder is mixed with Ti powder (A) and the ratio by volume of the resulting material of the biogenic material powder is set to 50% or less of the resulting sintered product after the mixed powder is sintered; and the biogenic material powder (B) for a surface layer portion is hydroxyapatite (HAp) powder, or tertiary calcium phosphate (β-TCP) powder.

5. The process for producing a concentric-circular-gradient functional material for biogenic use according to of claim 1, wherein the plurality of cylindrical projections are concentric circular and stepwise concaves having sizes permitting the respective cylindrical partitions to be fitted therein.

6. The process for producing a concentric-circular-gradient functional material for biogenic use according to of claim 1, wherein the plurality of cylindrical projections define concentric circular grooves having sizes permitting the respective cylindrical partitions to be fitted therein.

7. A process for producing a concentric-circular-gradient functional material for biogenic use, comprising:

standing 4 or more cylindrical partitions having diameters different from each other concentrically on a supporting stand;

standing, outside the cylindrical partition having the largest diameter, a cylindrical dice concentrically;

filling a Ti powder (A) for a central portion into the cylindrical partition positioned at the center;

filling a biogenic material powder (B) for a surface layer portion into a space confined by the outside of the cylindrical partition having the largest diameter and the inside of the cylindrical dice;

filling a mixed powder comprising the Ti powder (A) for a central portion and the biogenic material powder (B) for a surface layer portion into each of the spaces confined by the cylindrical partitions, the mixed powder being a mixed powder wherein the blend ratio of the biogenic material powder (B) for a surface layer portion is made larger step by step from the inside to the outside;

pulling out the cylindrical partitions;

capping the upper of the cylindrical dice using a cylindrical punch;

overturning the dice and the supporting stand upside down;

removing the supporting stand;

capping the upper of the dice using a punch; and sintering the powders with which the inside of the dice and the punches is filled using a discharge plasma sintering machine, wherein the supporting stand has, on the upper side thereof, a plurality of cylindrical projections configured to permit the respective cylindrical partitions to stand therein.

8. The process for producing a concentric-circular-gradient functional material for biogenic use according to claim 7, wherein the number of the cylindrical partitions stood concentrically on the supporting stand is set to at least five.

9. The process for producing a concentric-circular-gradient functional material for biogenic use according to of claim 7, wherein carbon paper is arranged as a releasing agent on the inside of each of the dice and the punches.

10. The process for producing a concentric-circular-gradient functional material for biogenic use according to claim 7, wherein filling the Ti powder (A) for a central portion comprises filling only Ti powder (A), or filling a mixed powder in which a biogenic material powder is mixed with Ti powder (A) and the ratio by volume of the resulting material of the biogenic material powder is set to 50% or less of the resulting sintered product after the mixed powder is sintered; and the biogenic material powder (B) for a surface layer portion is hydroxyapatite (HAp) powder, or tertiary calcium phosphate (β-TCP) powder.

11. The process for producing a concentric-circular-gradient functional material for biogenic use according to claim 7, wherein the plurality of cylindrical projections are concentric circular and stepwise concaves having sizes permitting the respective cylindrical partitions to be fitted therein.

12. The process for producing a concentric-circular-gradient functional material for biogenic use according to claim 7, wherein the plurality of cylindrical projections define concentric circular grooves having sizes permitting the respective cylindrical partitions to be fitted therein.

* * * * *